United States Patent [19]

Bringhurst et al.

[11] Patent Number: Plant 5,268

[45] Date of Patent: Aug. 7, 1984

[54] STRAWBERRY PLANT 'SANTANA'

[75] Inventors: Victor Voth, Santa Ana, Royce S. Bringhurst, Davis, both of Calif.

[73] Assignee: The Regents of the University of California, Berkeley, Calif.

[21] Appl. No.: 452,698

[22] Filed: Dec. 23, 1982

[51] Int. Cl.[3] ..... A01H 5/03

[52] U.S. Cl. ..... Plt./48

[58] Field of Search ..... Plt./48

*Primary Examiner*—Robert E. Bagwill

*Attorney, Agent, or Firm*—Townsend and Townsend

[57] ABSTRACT

A new and distinct variety of strawberry plant of the short-day type primarily characterized as the earliest fruiter of all California short-day varieties. The fruit is medium to short conic, slightly hollow internally with a firmness and durability about the same as 'Tufts', 'Tioga' and 'Aiko'. Fruit size is about the same as 'Tioga' and has a flavor comparable to most California varieties in use. The variety is suitable for both fresh and processing markets.

3 Drawing Figures

DESCRIPTION

This invention relates to a new and distinctive short-day type strawberry cultivar designated as 'Santana' which is the result of a cross between Cal 72.309-601 (not patented) and Cal 72.349-605 (not patented) made in 1977 as follows:

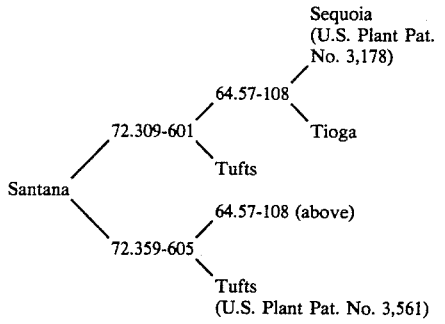

'Santana' first fruited at the University of California South Coast Field Station, Santa Ana in 1979 where it was selected and designated originally as Cal 77.36-604. It was tested later as advanced selection C6.

'Santana' has been propagated asexually by runners and has been tested at various University of California field stations and facilities and to a very limited extent in a few growers' fields under Test Agreement.

Figure 1:
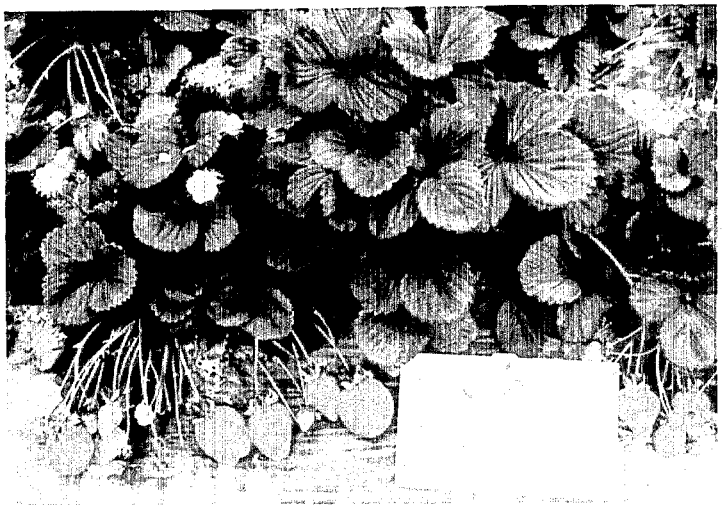
FIG. 1 shows typical growth, flowering and fruiting characteristics of the plant.
Figure 2:
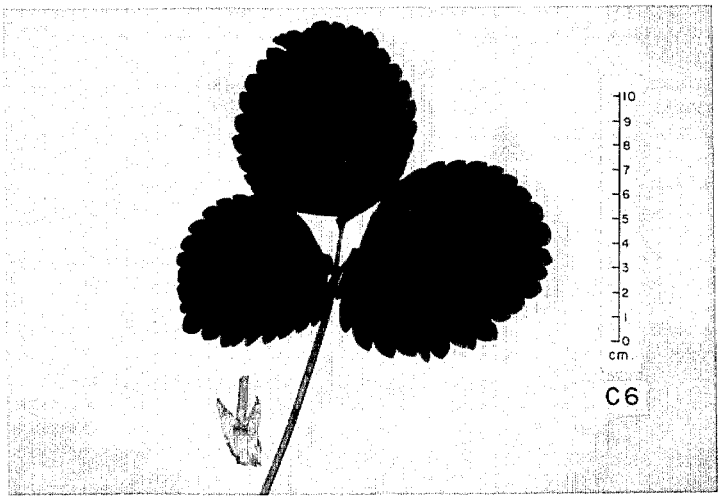
FIG. 2 shows a typical midsummer mature leaf from a plant in full fruit.
Figure 3:
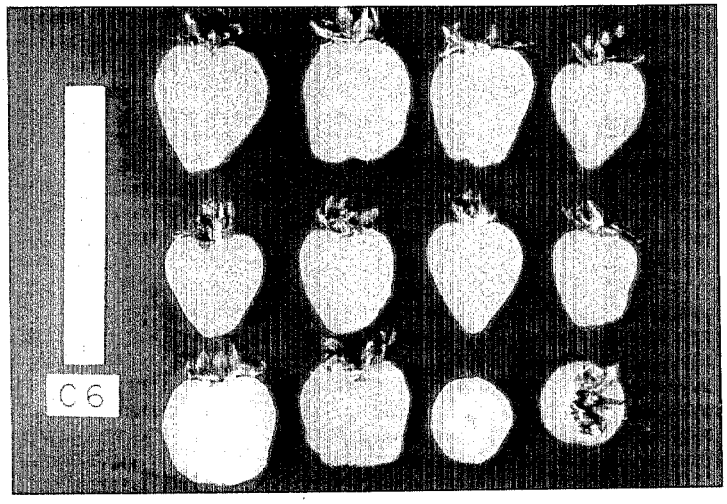
FIG. 3 shows representative early-season fruit with longitudinal and cross-sectional views.

'Santana' is early fruiting and has performed well in winter planting experiments, in south and central coastal California. It is the earliest fruiting of all of the California short-day type cultivars including 'Douglas'.

PLANTS AND FOLIAGE

'Santana' plants are erect in growth habit, and about the same size as those of the standard 'Tioga' in both winter and summer plantings as estimated by measuring petiole length on plants in full fruit. Leaflets of 'Santana' are about the same size as those of 'Tioga' and with about the same number of serrations. Leaves are less yellow and more intense than those of 'Tioga', 5GY5.6 vs 2.5GY4/3, respectively (Munsell Color System-Nickerson Color Fan). Runner production in nursery plantings is very good, better than 'Tioga'.

ISOZYMES IN LEAF EXTRACTS

'Santana' has been classified for three enzyme systems: (A) Phosphoglucoisomerase (PGI); (B) Leucine amino peptidase (LAP); and (C) Phosphoglucomutase (PGM), making it unique among California cultivars.

| | 'Tioga' | 'Tufts' | 'Douglas' | 'Pajaro' | 'Aiko' | 'Santana' |
|---|---|---|---|---|---|---|
| PGI | A1 | A2 | A3 | A4 | A4 | A3 |
| LAP | B1 | B3 | B3 | B3 | B3 | B1 |
| PGM | C3 | C4 | C1 | C1 | C2 | C1 |

*1981 J. Amer. Soc. Hort. Sci 106: 684–687.

FLOWERING AND FRUITING

'Santana' flowers are borne on fairly long, semi-erect peduncles which are brought down quickly by the weight of the fruit. The flowers are self fertile with ample pollen throughout the season and consequently there is little malformed fruit.

FRUIT APPEARANCE

'Santana' fruit is medium to short conic. Internally the fruit is usually slightly hollow. The fruit skin color is about 7R4.5/13 (ibid), slightly darker than that of fully colored 'Tioga' (about 7.5R4.5/13). The finish is glossy and attractive. The flesh is about the same color with a somewhat lighter ring around the core. The achenes are bright yellow, positioned flush with surface to slightly exserted. The calyx is medium in size positioned from slightly reflexed. The fruit is about as firm and durable as that of 'Tioga', 'Tufts' or 'Aiko' according to penetrometer readings and handling comparisons. The fruit size averages about as large as that of 'Tioga' with a wide range in size as the season advances.

FRUIT QUALITY

'Santana' has averaged higher ascorbic acid content (31 mg/100 g fresh fruit) than 'Tioga' (23) or 'Tufts' (27), 'Douglas' (28), but lower than 'Pajaro' (36) and 'Aiko' (41), as tested on summer and winter plantings during 1981 and 1982 by the method of Loeffler and Ponting (1942, J. Indust. an Engin. Chem. 14:846). Soluble solids readings were not significantly different from those of 'Tioga', 'Tufts', 'Aiko' or 'Pajaro' from comparable plantings. The flavor of 'Santana' is very good, comparable to that of most of the cultivars now used in California in our opinion and according to most who have tried it. It is suitable for fresh market and processing.

We claim:

1. The new and distinct variety of strawberry plant herein described and illustrated and identified by the characteristics enumerated above.

* * * * *